US 6,559,939 B1

(12) United States Patent          (10) Patent No.:     US 6,559,939 B1
Saunders                            (45) Date of Patent:     May 6, 2003

(54) METHOD OF HIGH THROUGHPUT HAZE SCREENING OF MATERIAL

(75) Inventor: Dennis L. Saunders, San Dimas, CA (US)

(73) Assignee: Avery Dennison Corporation, Pasadena, CA (US)

( * ) Notice: Subject to any disclaimer, the term of this patent is extended or adjusted under 35 U.S.C. 154(b) by 88 days.

(21) Appl. No.: 09/844,527

(22) Filed: Apr. 27, 2001

Related U.S. Application Data

(63) Continuation-in-part of application No. PCT/US00/29854, filed on Oct. 30, 2000.
(60) Provisional application No. 60/162,349, filed on Oct. 29, 1999.

(51) Int. Cl.⁷ .............................................. G01N 21/47
(52) U.S. Cl. ..................... 356/239.1; 356/443
(58) Field of Search .............................. 356/239.1, 443, 356/444, 124.5, 446

(56) References Cited

U.S. PATENT DOCUMENTS

| | | | |
|---|---|---|---|
| 4,623,258 A | | 11/1986 | Task et al. |
| H220 H | * | 2/1987 | Vogel ...................... 356/124.5 |
| 4,679,917 A | | 7/1987 | Genco et al. |
| 4,687,338 A | | 8/1987 | Task et al. |
| 4,804,274 A | | 2/1989 | Green |
| 5,155,558 A | | 10/1992 | Tannenbaum et al. |
| 5,198,869 A | | 3/1993 | Monteverde et al. |
| 5,218,417 A | | 6/1993 | Gay et al. |
| 5,451,524 A | * | 9/1995 | Coble et al. ................. 435/301 |
| 5,621,520 A | * | 4/1997 | Hoffman .................... 356/124.5 |
| H1655 H | | 6/1997 | Task |
| 5,712,709 A | | 1/1998 | Task et al. |

FOREIGN PATENT DOCUMENTS

| | | | |
|---|---|---|---|
| DE | 199 55 556 | * | 6/2000 |
| WO | WO 92/07248 | | 4/1992 |

OTHER PUBLICATIONS

*Standard Test Method for Measuring Halation of Transparent Parts*; Aug. 1990; American Society for Testing and Materials; Designation: F 943–90; pp. 668–671.
*Standard Test Method for Haze and Luminous Transmittance of Transparent Plastics*; Apr. 1998; American Society for Testing and Materials; Designation: D 1003–97; pp. 1–6.

* cited by examiner

Primary Examiner—Richard A. Rosenberger
(74) Attorney, Agent, or Firm—Oppenheimer Wolff & Donnelly LLP

(57) ABSTRACT

Disclosed are apparatus and associated methods for determining haze for various materials. More particularly, an efficient, high throughput screening methodology for the determination of haze of a plurality of materials is provided whereby contrast reduction characteristics of materials are utilized to determine haze. When utilized with a plurality of materials displayed in an array on a carrier, the present invention provides a substantive increase in the rate of discovery of haze characteristics of materials.

18 Claims, 4 Drawing Sheets

METHOD OF HIGH THROUGHPUT HAZE SCREENING OF MATERIAL

RELATED PATENT APPLICATION

This application is a continuation-in-part of a previously filed PCT Patent Application Serial Number PCT/US00/29854 filed Oct. 30, 2000, which in turn claims priority from prior U.S. Provisional Patent Application Serial No. 60/162,349 filed Oct. 29, 1999. Both of these disclosures are hereby incorporated in their entirety by reference.

BACKGROUND OF THE INVENTION

1. Field of the Invention

The present invention relates broadly to measuring haze of materials, such as coatings or films. More particularly, the present invention and associated methods are directed to high throughput methodologies for screening a plurality of materials in order to efficiently and rapidly ascertain characteristic-properties of materials, in particular, haze.

2. General Background and State of the Art

Materials display a wide range of characteristics that depend upon the various components that go into or make up particular materials. An exemplary, abbreviated list of the various characteristics that a material may display includes mechanical, thermal, chemical, electrical and optical properties. Many of these categories of characteristics may be further subdivided into other, more specific categories. For example, a plethora of additional descriptive categories fall within the more general category of optical characteristics. These include luminance, color, illuminance, brightness, transmission and absorption of various wavelengths of energy, reflectance and haze. The present invention is concerned with providing a novel and improved apparatus and associated methods of use that provides the expeditious determination of haze characteristics of a plurality of materials differing in their compositions.

Light that impinges upon materials may be reflected, absorbed, scattered or transmitted. Accordingly, the amounts and quantities of the various components that make up a material affect the manner in which light behaves when falling onto and/or through it. For example, certain components may scatter light more readily than other components. Similarly, other components of the materials may impart certain chromatic characteristics that absorb or reflect light in a manner, for example.

Certain specific characteristics, some of which have been previously mentioned, may be especially critical for a particular use or function of a material. For example, the haze characteristics of various materials or compounds are an important aspect of the design of many products. Haze is defined by the American Society for Testing and Material as "the scattering of light by a specimen responsible for the reduction in contrast of objects viewed through it" (ASTM D 1003-97).

The importance of the haze characteristic of various materials is the focus of much research and development in many industries. For example, the manufactures of various glasses and other light transmitting materials vary and optimize the optical properties of their products commensurate with their intended applications. Windshields, mirrors and other parts utilized in, the automobile manufacturing industry are continually being redesigned and optimized in regards to their various optical characteristics. In some instances, windows, of automobiles may contain, as part of their assembly, coatings or compounds on the surface of the windows, sandwiched in laminated glass sheets or within the glass proper, that are designed to reduce penetration of the UV portion of the light spectrum. This is in order to attenuate the bleaching effects of these wavelengths on fixtures found within the automobile's interior, for example.

Similarly, manufacturers of eyewear, photographic lenses, windows, CRTs, and light filters, as well as other products, have an interest in the manner in which their products interact with light. In many instances, this light interaction provides a particular protective and/or functional role. In the case of eyewear, manufactures must provide lenses that blocks UV radiation while at the same time having an upper limit to the haze of the lens, in order to provide users with clear images when the eyewear is worn. Similarly, photographic lenses may have filters placed between them and subjects of interest in order to impart a photographic effect. The haze characteristics of these filters play a significant role in the way in which the subject is captured and ultimately portrayed in the final image.

These and other examples make clear that haze is an optical property that has relevance in wide ranging fields. The prior art standard of measuring haze utilizes a Gardner Haze Meter. In this prior art methodology, the amount of light transmitted through a material and the amount of light scattered by the same material are utilized in an equation wherein the ratio of scattered to the total amount of light that comes through the material results in a haze value.

The prior art instrumentation for assessing the haze of various materials is limiting in a number of significant aspects. Prior art methodologies are slow, often requiring a substantial amount of time, one minute or more, to assess the haze of a single material. As one skilled in the art will appreciate, this rate of material assessment results in a limitation of the amount of materials that may be tested for haze characteristics over a given amount of time. While many hundreds of materials may be formulated utilizing automated means in a research and development laboratory, the bottleneck created by the limited number of samples that may be tested efficiently presents an area of major concern.

INVENTION SUMMARY

Therefore the present invention provides an apparatus and methods that greatly increase the rate at which material may be screened for haze characteristics. In conjunction with combinatorial chemistry methods that produce hundreds, even thousands of new materials per day, the present invention overcomes the previously stated disadvantages. The present invention provides a high throughput screening method and apparatus for haze that is capable of efficiently screening a plurality of materials. In an exemplary configuration, the present invention provides users with the ability to screen 750 samples of materials per hour. This provides a concomitant increase in the rate of discovery of materials that display particular haze characteristics, as well as determining the haze of newly formulated material in general.

The present invention provides users with the capability of measuring the haze of a plurality of sample materials disposed upon a substrate in an array configuration. An illustrative method, in accordance with the present invention includes disposing upon a substrate a plurality of materials utilizing a multi-well apparatus comprising an apertured top layer placed upon a bottom, substrate layer in order to form a plurality of material receiving wells. Material to be characterized is placed into the material receiving wells and processed. Material may be deposited into the material receiving wells by various techniques, including, but not limited to, pipettes, drip nozzles or sprayed, for example, when the materials are in liquid form. These techniques may also be automated. Exemplary processing of the material may include drying and centrifugation of the assembly in order to flatten the materials in the wells upon the substrate. Once processed, the apertured top layer is removed, exposing the bottom substrate layer with the material now disposed in an array. The array of samples may be formed by other techniques.

Both layers can be flexible, with the second or bottom layer being detachable from the overlying first layer, as previously mentioned. Such an apparatus can be made of disposable material, thus providing a cost-effective, efficient and reliable means of making and testing numerous formulations of material for haze characteristics.

The present invention utilizes a novel method of determining the reduction in contrast of a target in order to determine the haze of material. A target is provided having a background with indicia disposed upon it. The contrast of the indicia against the background is then determined. The target is next viewed through a haze calibration filter having a pre-selected haze value. The reduction in contrast, as viewed through a haze calibration filter, between the background and indicia is noted. The contrast values of the target as viewed directly and as viewed through the calibration filter, are utilized to calculate a haze calibration factor. The haze calibration factor will then be utilized in subsequent calculations to determine the haze of each material disposed in the array configuration.

After determining the haze calibration factor, the target is then viewed through the array of material disposed upon the substrate. At each location where sample material is disposed, the reduction in contrast between the background and indicia comprising the target, as viewed through the material on the substrate, is determined for every sample of the material in the array. These contrast values will comprise part of the equations utilized in order to determine the haze of each material. In this exemplary configuration, with a plurality of sample materials disposed upon a substrate, the substrate itself contributes a component to this contrast reduction and thus the initial calculated haze value of the material. This substrate haze component must be determined in order to obtain the corrected or "true" haze value of the material alone.

Therefore, the target is also viewed through the substrate material itself and the contrast between the background and indicia of the target is determined, as viewed through the substrate. This contrast, in addition to the haze calibration factor previously determined, is utilized to calculate haze of the substrate alone.

The haze of the samples of material disposed in an array on the substrate is then calculated by subtracting the haze value of the substrate from the initial haze value calculated for the sample material that is disposed upon the substrate. This is carried out for each of the plurality of sample material disposed upon the substrate. The values may be entered into a spreadsheet that is configured to efficiently and rapidly determine the haze of a plurality of materials. A more detailed description of the exemplary methods utilized by the present invention is provided below.

In accordance with one aspect of the invention an imaging device such as a video or still camera may capture images of an array of samples and underlying target which are appropriately illuminated, as part of the high throughput haze measuring system.

Other features and advantages of the present invention will become apparent from the following detailed description, taken in conjunction with the accompanying drawings, which illustrate, by way of example, the principals of the present invention.

DETAILED DESCRIPTION OF THE PREFERRED EMBODIMENTS

The high throughput method and associated apparatus of the present invention are designed for determining haze. The methods and apparatus provided minimize the time required to assess haze characteristics of a plurality of materials while increasing the rate of discovery of materials having pre-selected or desired haze properties, as well as determining the haze of materials in general. While the specification describes particular embodiments of the present invention, those of ordinary skill can devise variations of the present invention without departing from the inventive concepts.

Figure 1:
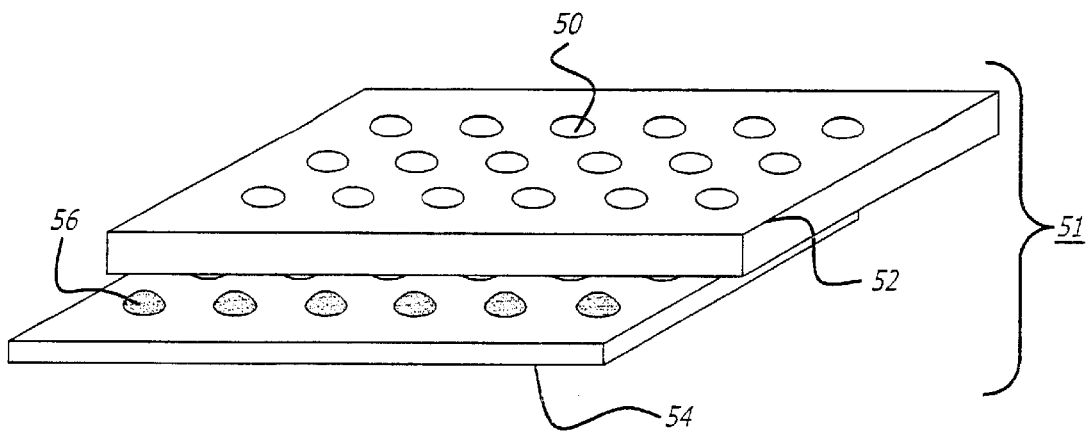
FIG. 1 is a side elevational view of the separated components of the multi-well apparatus comprising an apertured top layer and a bottom, substrate layer with a plurality of sample materials arranged in an array.
Figure 2:
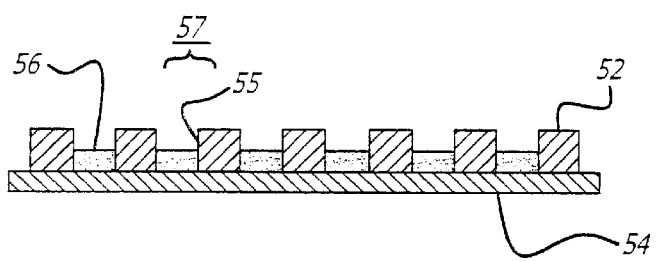
FIG. 2 is a cross sectional view of the two layered multi-well apparatus comprising an apertured top layer disposed upon a bottom, substrate layer with a plurality of materials deposited into material receiving wells.

Referring now to the drawings, more particularly FIG. 1, there is illustrated the components of a multi-well apparatus 51 that are utilized to arrange material in an array configuration. The top portion is comprised of a template top, or apertured sheet 52. Apertured sheet 52 may have a plurality of apertures 50 arranged in a convenient pattern, such as the exemplary patterns shown. Apertures 50 will form the wall portions 55 of material receiving wells 57, which are formed upon placing apertured sheet 52 onto a substrate 54, as seen in FIG. 2. In this exemplary depiction, apertures 50 are arranged in order to provide an array of materials in a plurality of columns and rows disposed upon a substrate, as detailed below. While the exemplary illustration of FIG. 1 provides eighteen apertures that will, form part of eighteen material receiving wells, apertured sheet 52 may be provided with many tens and even hundreds or thousands of apertures in order to provide a large number of material samples in useful arrangements. It is contemplated that apertures 50 may also be arranged in other configurations, such as circular, farther or more closely adjacent to one another, which are useful and commensurate with the methods of the present invention. Additionally, it is noted that apertures 50 are shown here as being circular, typically of about 1 cm in diameter, but other useful shapes may also be employed, such as square or rectangular apertures, as well as others.

Apertured sheet 52 may be comprised of a variety of materials. These include, but are not limited to paper, plastic, various rubbers, as well as various films. The selection of the particular material that apertured sheet 52 may be comprised of may depend upon the type of material to be screened. For example, the deposition of liquid samples into the material forming wells 57 in FIG. 2, may require apertured sheet 52 to be comprised of a material, such as rubber, that will contain the sample material in the material receiving well 57 and prevent leakage and cross contamination of the plurality of sample materials placed in each of the material receiving wells 57.

Still referring to FIG. 1, a second component of multi-well apparatus 51 is the substrate 54. Apertured sheet 52 is placed upon substrate 54 in tight engagement in order to form the material receiving wells. Substrate 54 forms the bottom portion of material receiving wells and will serve as a carrier for material to be screened. For example, substrate 54 may be a piece of polyethylene terephthalate (PET) film, about 0.5–7.0 mils thick. Substrate 54 may be comprised of other various materials, including other types of plastics, films or even glass. The selection of material of which substrate 54 will be comprised of may take into account properties, for example, corrosive or reactive, of the sample material that will be disposed upon substrate 54. For example, it may be advantageous that the material placed into material forming wells 57, be subjected to various processing steps. These steps may include, but are not limited to, centrifugation, drying, and exposure to various atmospheres and temperatures, for example. It is important to note that these conditions would necessitate selecting apertured sheet 52 and substrate 54 that will handle the prescribed conditions and procedures that the sample material will be subjected to.

FIG. 1 also depicts an example of material 56, as it may appear disposed upon substrate 54. In this figure, apertured sheet 52 is shown removed from substrate 54 after having been in engagement with substrate 54 and having material placed into the material receiving well thus formed, as detail earlier. Once sample material 56 has been processed and is ready for screening, apertured sheet 52 is separated from substrate 54, thus exposing a plurality of discrete sample material 56, now disposed upon substrate 54 in an array.

A cross sectional view of the multi-well apparatus 51, with apertured sheet 52 placed upon substrate 54, is shown in FIG. 2. In this view, sample material 56 is seen within the material receiving wells 57 formed by apertured sheet 52 and substrate 54 when placed upon one another. As mentioned previously, the apertures 50 of apertured sheet 52 form the sidewalls 55 of the aforementioned material receiving wells 57.

Figure 3:
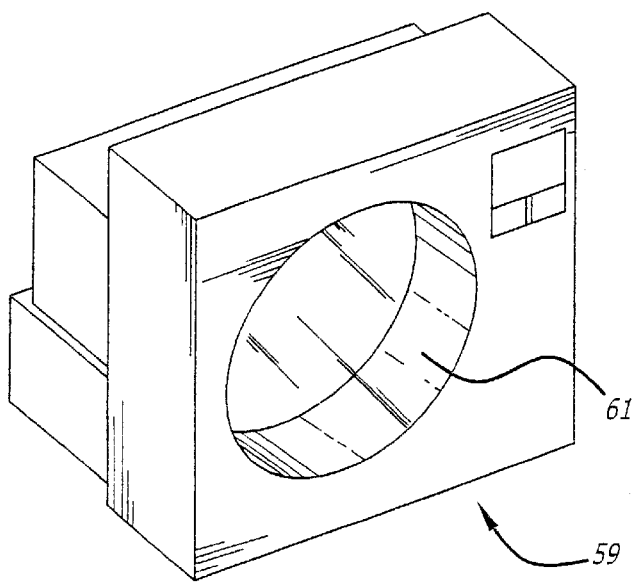
FIG. 3 is a perspective view of a centrifuge usable in an exemplary embodiment of the invention.
Figure 4:
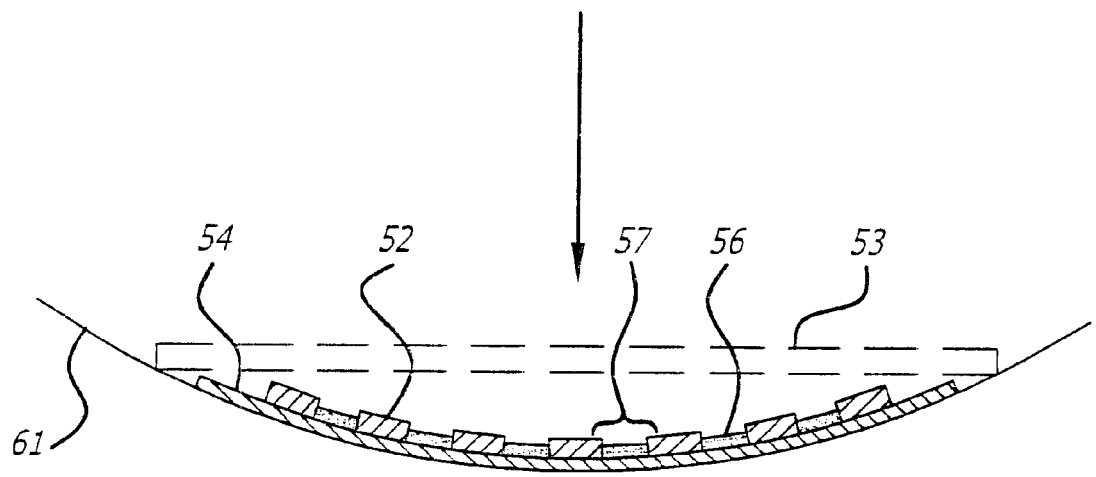
FIG. 4 is a schematic cross sectional, internal view of a centrifuge wherein a flexible multi-well apparatus having a flexible, apertured sheet and flexible substrate are mounted with a plurality of materials deposited into material receiving wells.

Once material has been placed into the plurality of material receiving wells provided by multi-well apparatus 51, the material may be subjected to various processing procedures. In order to provide flattened samples, the multi-well apparatus 51 may be placed into a centrifuge, as seen in FIG. 3. It is important to note that in order for the materials to flatten upon substrate 54 and not climb up the well walls and form meniscuses, the curvature adopted by the multi-well apparatus 51 during centrifugation will substantially match the curvature of the curvilinear path of the centrifuge rotor, as depicted in FIG. 4. The type of centrifuge that is particularly well suited for these purposes is of the "drum-type" centrifuge of which is depicted in FIG. 3. Here, the axis of rotation is horizontal, similar to a front loading clothes dryer, and multi-well apparatus 51 with material 56 placed in its material receiving wells 57 is mounted onto the centrifuge's curved, rotating surface 61, as detailed below.

In FIG. 4 a cross section is provided wherein a multi-well apparatus 51 with material 56 placed in its material receiving wells 57, is being centrifuged. The top, apertured sheet 52 as well as substrate 54 are here comprised of flexible material. As stated previously, an exemplary apertured sheet 52 may be made from various rubbers, such as silicon rubber. Flexibility is likewise imparted upon substrate 54 if, for example, PET film is utilized as the substrate 54. Thus, when multi-well apparatus 51 is first placed into a centrifuge it may maintain its linear profile, as depicted by the dashed lines 53. However, when the centrifuge is activated and the centrifugal force, as depicted by the arrow in FIG. 4, acts upon the flexible multi-well apparatus 51, it will flex to match the rotating surface 61 and curvilinear pathway of the rotating surface 61. This places material 56 in all of the wells at the same distance from the spin axis of the centrifuge resulting in consistent profiles of all materials 56 disposed upon substrate 54.

Figure 5:
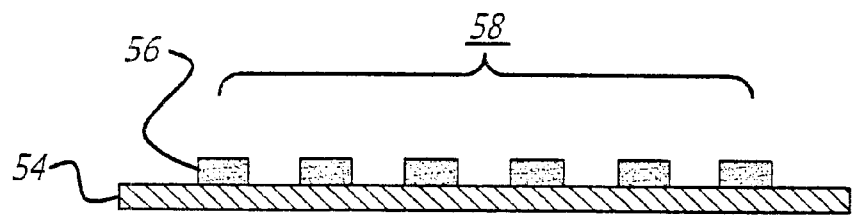
FIG. 5 is a cross sectional view of a plurality of materials disposed upon a substrate.

Turning now to FIG. 5, a cross sectional view of a plurality of sample material 58 disposed upon substrate 54 is depicted. As stated in the preceding text, once sample material 56 is disposed into material receiving wells 57 and processed, apertured plate 52 is separated from substrate 54, thus displaying an array of sample material 58. With the array of sample material 58 thus exposed, the haze of each sample material 56 in the array may be determined, as detailed below.

Figure 6:
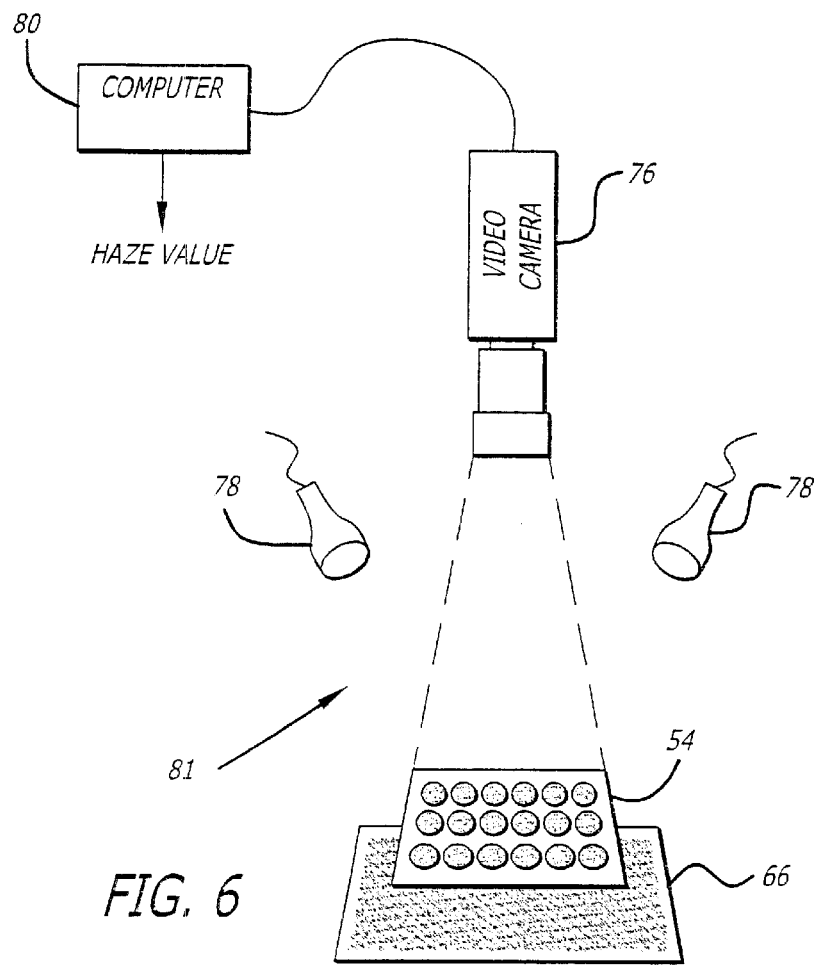
FIG. 6 is a schematic side view of a system utilized for the high throughput method of measuring haze of a plurality of materials disposed upon a substrate.

An exemplary, schematic representation of the system 81 utilized for performing high throughput haze screening is illustrated in FIG. 6. The high throughput haze screening system is configured to provide the rapid determination of haze of a plurality of materials disposed in an array upon substrate 54. System 81 is comprised of a target 66 that has a background with indicia disposed thereon, a light source 78, an image capturing apparatus 76, and a computer 80. This schematic illustrates the setup of system 81 when determining the haze of a plurality of samples upon a substrate 54, which includes placing substrate 54 with sample material 56 thereon disposed above the target 66, and utilizing the image capturing apparatus 76 and computer 80 to capture and analyze areas of an image of target 66, as viewed through substrate 54 having sample material 56 thereon disposed.

System 81, in the exemplary configuration described herein, utilizes digital photography and image analyzing software to measure the contrast of the indicia disposed upon the background of target 54. The steps by which the present invention is practiced are detailed below.

The methods of the present invention are based upon measuring the contrast between indicia and a background. This will be referred to as the target 66. When the target is viewed through a hazy material, there is a quantitatively measurable change (decrease) in the contrast between the indicia and the background of target 66 compared to the contrast between the indicia and the background of target 66 when viewed directly (not through a hazy material). This contrast change is related to the haze of the material. The haze of the sample material is determined by reference to a haze calibration factor, utilizing haze calibration films of known haze values. If material 56 is disposed upon substrate 54, as depicted in the arrays previously mentioned, a correction for the haze that is inherent to the composition of substrate 54 itself is taken into account when image analysis of the target 66 is conducted. A more detailed description of the method of high throughput haze screening is described below.

In order for the system 81 to facilitate the high throughput methods for haze screening, a haze calibration factor must first be established. Recalling that the present invention utilizes the change (decrease) in contrast between indicia disposed upon a background when viewed through a material as an indication of the haze of that material, the haze calibration factor is determined by using films having known haze values. The subsequently quantitative measurements of haze of sample materials will be related to the known haze values of the calibration filters by the calibration factor, as detailed in the calculations below.

Figure 7:
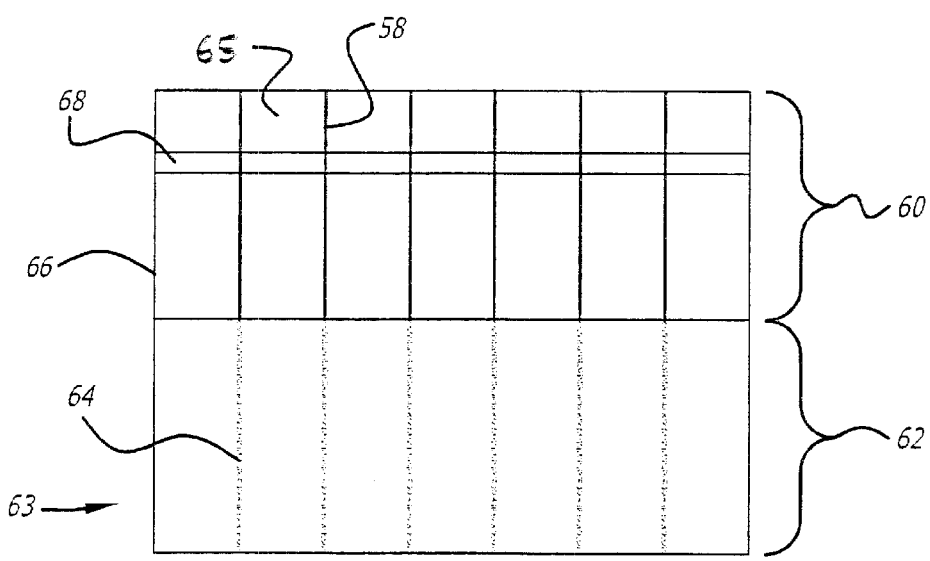
FIG. 7 is a captured image view of the target utilizing image analysis software, with a measurement line, as viewed directly (upper portion) as well as viewed through a haze calibration filter (bottom portion).
Figure 9:
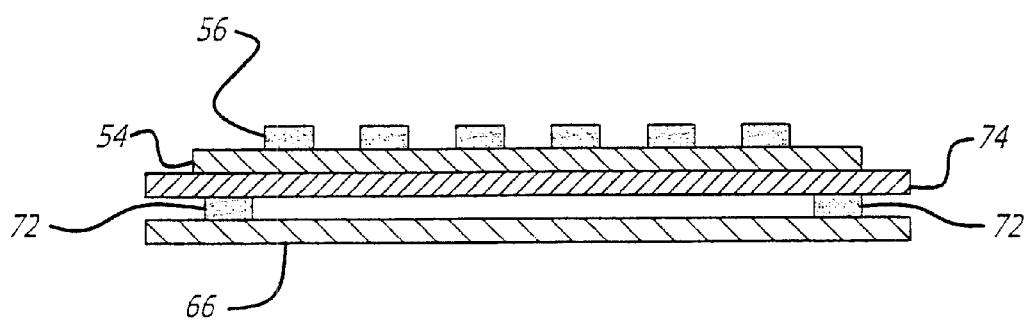
FIG. 9 is a cross sectional view of an exemplary configuration of the target area when measuring haze of a plurality of samples, with substrate having a plurality of materials disposed thereon, the substrate being placed on a support platform over the target.

An understanding of how the haze calibration factor is determined will be appreciated by referring to FIGS. 6, 7 and 9. Referring to FIG. 6, the target 66 is placed within the field of view of image capturing apparatus 76. A transparent plate, such as glass, may be placed over the target 66. Upon this plate or directly onto the target 66, spacers 72 may be placed, as seen in FIG. 9. Upon spacers 72 a transparent plate 74 may also be placed. This plate 74 upon the spacers 72 will serve as a support upon which the substrate 54 with material samples 56 may be placed.

The image capturing apparatus 76 may be a digital or standard camera or video camera. In the preferred embodiment, image-capturing apparatus 76 is a dark and light video camera connected to computer 80. It is also contemplated that a color image capturing apparatus 76 may be utilized, with the subsequent captured images undergoing various image analyses commensurate with methodologies disclosed herein, in order to determine the haze of materials.

After positioning and aligning the target 66, the image capturing apparatus 76 is focused and its settings are optimized. In the current exemplary configuration, image-capturing apparatus 76 (B/W video camera) utilizes a ⅟60 sec shutter, gain set at AGC and the light balance set to ATW. Exemplary computer software, here ImagePro, is utilized to control aspects of the capturing of images of target 66 and the subsequent image analyses. Default ImagePro software settings are utilized. The ImagePro brightness and contrast settings are both set to 39 and 8 bit grey scale acquisition is selected.

Referring in particular to FIG. 7, a calibration factor is determined by the following method. A calibration film 63 with a known haze value is placed over the lower half of the target 66. FIG. 7 depicts an image captured by the image capturing apparatus 76 (B/W video camera) of target 66, the target here comprising a set of dark lines 58 upon a light background 65. Two distinct areas are seen. In the top area 60 of the captured image, the target's 66 set of dark lines 58 upon a light background 65 are viewed directly. In the bottom area 62 of the captured image, the target's 66 set of dark lines 58 upon a light background 65 are seen as viewed through the haze calibration film 63.

Next the captured image, FIG. 7, is subjected to image analysis. In ImagePro's "Measure" menu, "Line Profile" is selected, followed by selecting "Thick Horizontal" in the "Line Profile" window "Report" menu. This brings up the measurement line 68 upon the captured image on the computer's monitor. The measurement line 68 is adjusted to reach from one end of the captured image to the other. The width of the measurement line 68 should be adjusted to the same width of dark lines 58 seen within the target 66. The measurement line 68, which is movable upon the captured image, selects the areas of the captured image that the software will scan and assign intensity values.

The measurement line 68 in the captured image is first positioned in an area of the target 66 which is viewed directly 60. When thus positioned, the predominant baseline light signal of intensity of the light background 65, as viewed in the "Line Profile" window, should be between 225–250. If it is not, the aperture of the image capturing apparatus 76 (B/W video camera) is adjusted. In similar fashion, the intensity of the pixels in the area of the dark lines 58 in the captured image of the target should be above zero but below 30. The image displaying these proper dark and light intensity values is the calibration image. All of the settings used for this calibration must be also utilized in all images of sample material.

The software scans the portion of the captured image, displayed on the computer's monitor, which is demarcated by the measurement line 68. With the settings adjusted as previously described, the software scans across the captured image of the target 66, generating a set of numbers corresponding to the intensity differences between the light background 65 and dark lines 58, in the area of the target viewed directly 60. This gives a contrast value according to the equation:

$C_0 = W_0 - B_0$ where $C_0$ is the contrast (difference) between the maxima of the intensity of the light area ($W_0$) and the minima of the intensity of the dark area ($B_0$) of the target 66 when viewed directly.

Next, still referring to the captured image depicted in FIG. 7, the measurement line 68 is moved into the bottom portion 62 of the captured image. As stated previously, this portion of the captured image is of the target 66 as viewed through a calibration filter 63 having a known haze value. The software scans this second portion of the image and generates a set of numbers corresponding to the intensity differences between the light background 65 and dark lines 58 in this area. The contrast of this area is likewise determined using the equation:

$C_X = W_X - B_X$ where $C_X$ is the contrast (difference) between the maxima of the intensity of the light area ($W_X$) and the minima of the intensity of the dark area ($B_X$) of the target 66 in the lower portion 62 when viewed through the haze calibration filter 63.

These two values ($C_0$ and $C_X$) are utilized to calculate the haze calibration factor (f) according to the equation $$f = \frac{H}{\log\left(\frac{C_0}{C_X}\right)};$$

where H is the known haze of the haze calibration film through which the target 66 is viewed, as detailed above.

It is this haze calibration factor that will be utilized to calculate the haze of sample materials in subsequent captured images of the target 66 as viewed through the sample material. The previously detailed calculations, as well as additional operations detailed below, may be accomplished more efficiently by utilizing spreadsheet software programs.

Once the haze calibration factor has been thus determined, the next step is to measure the changes in contrast between the light background 65 and dark lines 58 of target 66, as viewed through a plurality of discretely disposed materials upon a substrate. This will be more easily understood by referring now to FIGS. 8 and 9.

Figure 8:
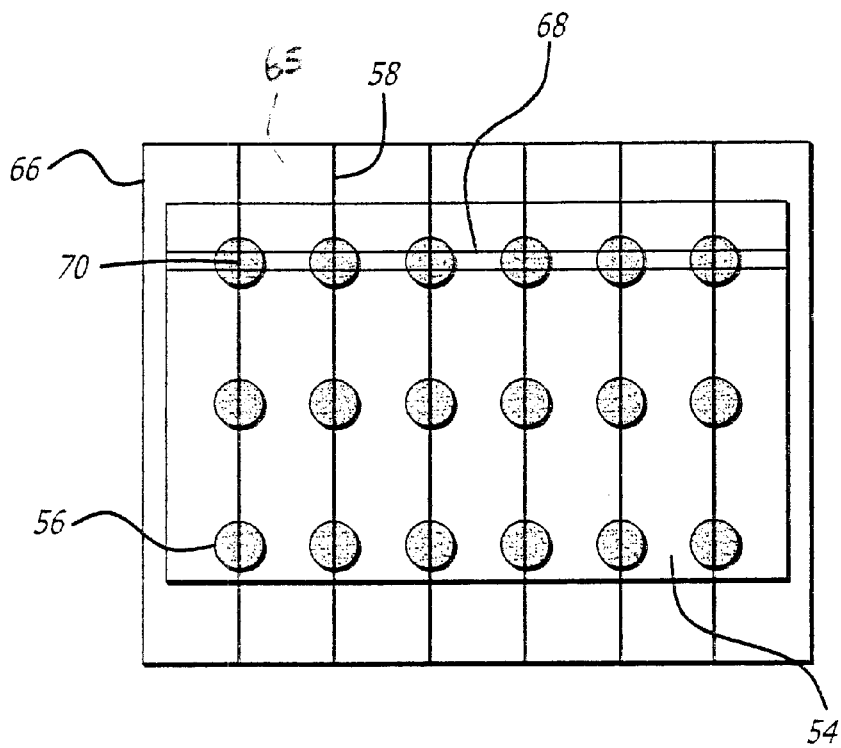
FIG. 8 is a captured image view of the target utilizing image analysis software, as it appears when viewed through a plurality of materials placed upon a substrate.

FIG. 8. illustrates a cross sectional view of an exemplary configuration of the target 66 with substrate 54 with sample material 56 disposed in an array. Substrate 54 is placed over the target 66 with substrate 54 resting on a transparent support 74, which is in turn supported by spacers 72. This arrangement provides the ability to view and capture an image of the target 66 as viewed through a plurality of sample materials 58, as described below.

FIG. 8 depicts a captured image, as may be seen on the computer's 80 monitor, of the target 66 as viewed through a substrate 54 having an array of material 56 thereon disposed, as configured in FIG. 8. It is important to note that multiple samples of material 67 are arranged so as to be aligned with the dark lines 58 of target 66. As a result, the contrast between the dark lines 58 and light background 65, as viewed through the material 56, is reduced. The image analysis software's measurement line 68, with the same settings utilized to calculate the haze calibration factor, is used to scan the captured image, as detailed previously. The software scans each sample containing position of the image and generates a set of numbers corresponding to the intensity differences 70 between the light background 65 and dark lines 58 as viewed through each sample 56 disposed upon substrate 54.

The haze of each sample is then calculated accordingly. The measurement line 68 is positioned in the image so as to run through each row of sample material 56 as disposed upon the substrate. The reduced contrast ($C_S$) (difference) between the maxima of the intensity of the light area ($W_S$) and the minima of the intensity of the dark area ($B_S$) of the target 66 as viewed through each sample is similarly calculated as detailed above, that is, $C_S=W_S-B_S$.

The determination of the haze of each of the samples ($H_S$) may now be determined by the following equation, which utilizes the haze calibration factor (f), contrast ($C_S$) (difference) between the maxima of the intensity of the light area ($W_S$) and the minima of the intensity of the dark area ($B_S$) of the target 66 as viewed through each sample, as well as ($C_O$), the contrast (difference) between the maxima of the intensity of the light area ($W_O$) and the minima of the intensity of the dark area ($B_O$) of the target 66 when viewed directly:

$$H_S = f\log\left(\frac{C_0}{C_S}\right)$$

It is to be noted that if samples are disposed upon a substrate, the substrate's haze must also be calculated and subtracted from the haze calculated for the sample, in order to determine the "true" or corrected haze of the sample alone. Therefore, the measurement line 68, in a captured image such as depicted in FIG. 8, is moved to a portion of the image wherein the target is viewed solely through the substrate 54. As previously mentioned, the computer scans the image and determines the contrast ($C_{Substrate}$) (difference) between the maxima of the intensity of the light area ($W_{Substrate}$) and the minima of the intensity of the dark area ($B_{Substrate}$) of the target 66 as viewed through the substrate 54. This contrast is then used in the equation of the previous paragraph in order to determine the haze of the substrate ($H_{Substrate}$). The corrected haze for each of the sample material 63 is then simply provided by:

$$(H_{sample})=(H_{sample\ on\ substrate}-H_{substrate}).$$

In closing it is to be understood the embodiments of the present invention herein disclosed are illustrative of the principals of the invention. Other modifications may be employed which are within the scope of the invention; thus, by way of example but not limitation, alternative variations of the apparatus and associated methods of use may be utilized in the high throughput haze screening. For example, image capturing apparatus 76 may also be a camera that provides standard photographic prints which then may be scanned into a computer 80 for image analysis by way of a flatbed scanner. Likewise, it considered to be within the scope of the present invention to provide a target 66 with alternate patterns of indicia disposed upon a background, such as a plurality of dots, that may be utilized in the contrast measurements herein described. Further, the array of samples need not be formed as shown in FIGS. 1–5 of the drawings, but could be formed from a plurality of separately formed samples assembled and mounted on a substrate. Accordingly, the present invention is not limited to that precisely shown and described.

I claim:

1. A high throughput method for efficiently screening arrays of materials for haze, comprising the steps of:
   forming a series of material receiving receptacles or wells by providing a substrate and an overlying apertured sheet with said apertured sheet in tight sealing engagement with said substrate;
   applying different materials into said receptacles;
   placing said substrate with said material receiving receptacles thereon in a centrifuge;
   activating said centrifuge with said receptacles mounted therein to flatten said materials in said receptacles;
   removing said overlying apertured sheet to leave said materials exposed on said substrate, thus forming said array;
   providing a target comprising a background and indicia disposed thereon;
   determining the contrast between said background and indicia when viewed directly, as well as through a haze calibration film, to calculate a haze calibration factor;
   determining the contrast between said background and indicia when viewed through said materials disposed upon said substrate, as well as when viewed solely through said substrate; and
   determining the haze of said materials utilizing said calibration factor and contrasts as determined for said background and indicia when viewed through said materials disposed upon said substrate as well as when viewed solely through said substrate.

2. The high throughput method of claim 1, wherein said aptertured sheet and substrate are flexible.

3. The high throughput method of claim 1, wherein said haze calibration filter is comprised of a film of known haze.

4. The high throughput method of claim 1, wherein said target is comprised of dark lines on a light background.

5. The high throughput method of claim 1, wherein said determinations of contrasts, calibration factor, and haze are carried out by computer analysis utilizing images of said views of said target.

6. The high throughput method of claim 5, wherein said images are captured by a conventional or digital camera.

7. The high throughput method of claim 5, wherein said images are captured by a conventional or digital video camera.

8. A high throughput method for efficiently screening arrays of materials for haze, comprising the steps of:

forming a series of material receiving receptacles or wells by providing a substrate and an overlying apertured sheet with said apertured sheet in tight sealing engagement with said substrate;

applying different materials into said receptacles;

drying the materials;

removing said overlying apertured sheet to leave said materials exposed on said substrate, thus forming said array;

providing a target comprising a background and indicia disposed thereon;

determining the contrast between said background and indicia when viewed directly, as well as through a haze calibration film, to calculate a haze calibration factor;

determining the contrast between said background and indicia when viewed through said materials disposed upon said substrate, as well as when viewed solely through said substrate; and determining the haze of said materials utilizing said calibration factor and contrasts as determined for said background and indicia when viewed through said materials disposed upon said substrate as well as when viewed solely through said substrate.

9. A high throughput method for determining haze of sample material, said method comprising the steps of:

providing a target having a light background and dark indicia disposed thereon;

determining a first contrast $C_0$ between said indicia and said background when viewed directly; where $C_0=W_0-B_0$ where $W_0$ is the maximum intensity of the light background and $B_0$ is the minimum intensity of the dark indicia areas;

determining a second contrast Cx between said indicia and said background when viewed through a haze calibration filter;

calculating a haze calibration factor f from said first contrast and said second contrast using the formula $$f = \frac{H}{\log\left(\frac{C_0}{C_X}\right)}$$

where H is the known haze of the haze calibration filter;

determining a third contrast $H_S$ between said indicia and said background when viewed through sample material disposed upon a substrate, using the formula:

$$H_S = f \log\left(\frac{C_0}{C_S}\right)$$

determining a fourth contrast between said indicia and said background when viewed through said substrate alone; and calculating a haze value for said sample utilizing said calibration factor and said third and fourth contrasts as follows:

$(H_{sample}) = (H_{sample\ on\ substrate} - H_{substrate})$.

10. The high throughput method of claim 9, wherein said target is comprised of dark parallel lines on a light background.

11. The high throughput method of claim 9, wherein said determinations of contrasts, calibration factor, and haze are carried out by computer analysis utilizing images of said views of said target.

12. The high throughput method of claim 11, wherein said images are captured by a conventional or digital camera.

13. The high throughput method of claim 11, wherein said image is captured by a conventional or digital video camera.

14. The high throughput method of claim 9, wherein a plurality of sample material are discreetly disposed upon said substrate by:

forming a plurality of materials;

applying said plurality of materials onto a substrate; and thus forming an array of materials for which the haze of each may be determined.

15. A high throughput method for efficiently screening arrays of materials for haze, comprising the steps of:

forming a plurality of materials having different haze characteristics in an array configuration upon a substrate;

providing a target comprising a light background and dark indicia disposed thereon;

determining a first contrast $C_0$ between said indicia and said background when viewed directly; where $C_0=W_0-B_0$ where $W_0$ is the maximum intensity of the light background and $B_0$ is the minimum intensity of the dark indicia areas;

determining a second contrast Cx between said indicia and said background when viewed through a haze calibration filter;

calculating a haze calibration factor f from said first contrast and said second contrast using the formula $$f = \frac{H}{\log\left(\frac{C_0}{C_X}\right)}$$

where H is the known haze of the haze calibration filter;

determining a third contrast $H_S$ between said indicia and said background when viewed through sample material disposed upon a substrate using the formula $$H_S = f \log\left(\frac{C_0}{C_S}\right)$$

determining the relative haze of each of said materials in said array, utilizing said calibration factor and contrasts and the formulas as set forth above.

16. The high throughput method of claim 15, wherein said substrate is comprised of polyethylene terephthalate (PET) film.

17. The high throughput method of claim 15, wherein said target is comprised of dark parallel lines on a light background.

18. The high throughput method of claim 15, wherein said determination of contrasts and calibration factor are carried out by a computer utilizing image analyzing software, said computer measuring said contrasts from images of said views of said target, whereby the haze of said materials is determined.

* * * * *